United States Patent
Yamazaki et al.

(10) Patent No.: US 7,070,801 B2
(45) Date of Patent: Jul. 4, 2006

(54) SUGAR-MODIFIED LIPOSOME AND PRODUCTS COMPRISING THE LIPOSOME

(75) Inventors: Noboru Yamazaki, Tsukuba (JP); Shuji Kojima, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/352,914

(22) Filed: Jan. 29, 2003

(65) Prior Publication Data

US 2003/0143267 A1    Jul. 31, 2003

(30) Foreign Application Priority Data

Jan. 30, 2002    (JP) ............... 2002-022575
Jan. 30, 2002    (JP) ............... 2002-022576

(51) Int. Cl.
    *A61K 9/127*    (2006.01)
(52) U.S. Cl. ............... 424/450; 424/1.21; 424/9.321; 424/9.51; 424/417; 428/402.2
(58) Field of Classification Search ............... 424/450, 424/1.21, 9.321, 9.51, 417; 428/402.2
    See application file for complete search history.

(56) References Cited

U.S. PATENT DOCUMENTS

| | | | | |
|---|---|---|---|---|
| 4,721,612 A | * | 1/1988 | Janoff et al. | 424/1.21 |
| 5,243,035 A | * | 9/1993 | Nakabayashi et al. | 536/4.1 |
| 5,264,221 A | * | 11/1993 | Tagawa et al. | 424/450 |
| 5,354,853 A | * | 10/1994 | Staveski et al. | 536/17.1 |
| 5,686,103 A | * | 11/1997 | Redziniak et al. | 424/450 |
| 2001/0046970 A1 | | 11/2001 | Nagy et al. | |

FOREIGN PATENT DOCUMENTS

EP    0 677 295 A1    10/1995

OTHER PUBLICATIONS

Papahadjopoulos et al, Proc. Natl. Acad. Sci. USA, vol. 88, pp. 11460-11464, Dec. 1991.*
Yamazaki, N., Kojima, S., Gabius, S. & Gabius, H.-J. Studies on Carbohydrate-Binding Proteins Using Liposome-Based Systems-1. Preparation of Neoglycoprotein-Conjugated Liposomes and the Feasability of Their Use as Drug-Targeting Devices (1992) *Int. J. Biochem.* vol. 24, 99-104.
Yamazaki, N., Kodama, M. & Gabius, H.-J. (1994) *Methods Enzymol*. "Neoglycoprotein-Liposome and Lectin-Liposome Conjugates as Tools for Carbohydrate Recognition Research" vol. 242, 56-65.

(Continued)

*Primary Examiner*—Gollamudi S. Kishore
(74) *Attorney, Agent, or Firm*—Sughrue Mion, PLLC

(57) ABSTRACT

The present invention provides a sugar-modified liposome having a sugar chain bonded to its membrane surface, preferably through a linker protein, and having excellent absorption qualities, particularly in the intestine. The molecular structure and quantity of the sugar chain is selectively varied to allow the liposome to be delivered in a targeted manner to selected cells and tissues. The liposome is applicable to medicinal drugs, cosmetics and other various products in the medical/pharmaceutical fields, and it is especially useful in a therapeutic drug delivery system that recognizes target cells and tissues, such as cancer cells, and in the delivery of drugs or genes locally to a selected region, or in a diagnostic cell/tissue sensing probe.

15 Claims, 21 Drawing Sheets

OTHER PUBLICATIONS

Yamazaki, N., Kaihou, S., Gabius, H.-J. & Kojima, S. "Neoglycoprotein-Liposome Conjugates: Their Preparation and Applications" (1996) *Progress in Drug Delivery System* 5, 75-80.

Yamazaki, N. "Preparation of Neoglycoprotin-Liposome Conjugates and Their Applications for Studying Recognition Functions Based on Membrane-Surface Carbohydrate-Protein Interactions" (1998) *J. of NIMC*, vol. 6, No. 5, pp. 199-211.

Yamazaki, N., Jigami, Y., Gabius, H. -J., and S. Kojima "Preparation and Characterization of Neoglycoprotein-Liposome Conjugates: A Promising Approach to Developing Drug Delivery Materials Applying Sugar Chain Ligands" (2001) *Trends in Glycoscience and Glycotechnology* 13:319-329.

Deol et al. Lung Specific Stealth Liposomes: Stability, Biodistribution and Toxicity of Liposomal Antitubercular Drugs in Mice (1997) *Biochimica et Biophysica Acta* 1334: 161-172.

European Search Report dated Aug. 6, 2003.

* cited by examiner

SUGAR-MODIFIED LIPOSOME AND PRODUCTS COMPRISING THE LIPOSOME

FIELD OF THE INVENTION

The present invention relates to a liposome having a sugar chain bonded to its membrane surface, preferably through a linker protein, and having excellent qualities in intestinal absorption, and to a liposome product comprising a drug or a gene encapsulated in the sugar-modified liposome. The liposome product may be used in preparations comprising medicinal drugs, cosmetics and other various products in the medical/pharmaceutical fields, and it is particularly useful in a therapeutic drug delivery system that specifically targets selected cells or tissues, such as cancer cells, and in the delivery of drugs or genes locally to a selected region, and in a diagnostic cell/tissue sensing probe.

BACKGROUND OF THE INVENTION

The realization of a "drug delivery system (DDS) for delivering drugs or genes intentionally and intensively to cancer cells or target tissues" has been set as one of the specific goals of the U.S. National Nanotechnology Initiative (NNI). The Nanotechnology/Materials Strategy of the Council for Science and Technology Policy in Japan also focuses research on "Medical micro systems/materials, Nanobiology for utilizing and controlling biological mechanisms," and one of the five year R & D targets is "Establishment of basic seeds in health/life-lengthening technologies such as biodynamic materials and pinpoint treatments." However, even in view of these goals the incidence and morbidity of cancers become higher year after year, along with a progressive aging of the population, and a serious need for the development of a targeting DDS material which is a novel treatment material exists.

Targeting DDS nano-structured materials for other diseases also come under the spotlight because they have no side effects, and their market size of over 10 trillion yen is anticipated in the near future. Further, it is expected that these materials will be utilized in medical diagnosis as well as medical treatments.

The therapeutic effect of a drug will be achieved only if the drug reaches a specific target region and acts thereupon. If the drug reaches a non-target region, undesirable side effects may result. Thus, the development of a drug delivery system that allows drugs to be used effectively and safely is also desired. In a drug delivery system, the targeting DDS can be defined as a concept of delivering a drug to a "necessary region in a body," in a "necessary amount" and for a "necessary time-period." A liposome is a noteworthy particulate carrier regarded as a representative material for a targeting DDS. While a passive targeting method based on modification of lipid type, composition ratio, size, or surface charge of liposomes has been developed to impart a targeting function to this particle, this method is still insufficient and required to be improved in many respects.

An active targeting method has also been researched in an attempt to achieve a sophisticated targeting function. While the active targeting method referred to as a "missile drug" is conceptually ideal, it has not been accomplished in Japan and abroad, and future developments are expected. This method is designed to provide ligands bonded to the membrane surface of a liposome that will be specifically recognized and bound by a receptor residing on the cell-membrane surface of a target tissue, thereby achieving active targeting. The cell-membrane surface receptor ligands include antigens, antibodies, peptides, glycolipids, and glycoproteins.

It is revealing that the sugar chain of glycolipids and glycoproteins bears an important role as an information molecules in various communications between cells, such as in the creation or morphogenesis of tissues, in the proliferation or differentiation of cells, in the biophylaxis or fecundation mechanism, and in the creation and metastasis of cancers.

Further, research on various types of lectins (sugar-recognizing protein) such as selectin, siglec and galectin, which serve as receptors on cell-membrane surfaces of target tissues, has been proposed to serve as receptors for sugar chains having different molecular structures that may be used as noteworthy new DDS ligands (Yamazaki, N., Kojima, S., Bovin, N. V., Andre, S., Gabius, S. and H. -J. Gabius. *Adv. Drug Delivery Rev.* 43:225–244 (2000); Yamazaki, N., Jigami, Y., Gabius, H. -J., and S. Kojima. *Trends in Glycoscience and Glycotechnology* 13:319–329 (2001)).

Liposomes having ligands bonded to their external membrane surface have been actively researched in order to provide a DDS material for delivering drugs or genes selectively to a target region, such as cancer. While these liposomes bind to target cells in vitro, most of them do not exhibit adequate targeting to intended target cells or tissues in vivo (Forssen, E. and M. Willis. *Adv. Drug Delivery Rev.* 29:249–271 (1998); Takahashi, T. and M. Hashida. *Today's DDS/Drug Delivery System,* Iyaku Journal Co., Ltd. (Osaka, Japan), 159–167 (1999)). While some research has been conducted on liposomes incorporating glycolipids having sugar chains, for use as a DDS material, these liposomes were evaluated only in vitro, and little progress has been reported for similar research on liposomes incorporating glycoproteins having sugar chains (DeFrees, S. A., Phillips, L., Guo, L. and S. Zalipsky. *J. Am. Chem. Soc.* 118: 6101–6104 (1996); Spevak, W., Foxall, C., Charych, D. H., Dasgupta, F. and J. O. Nagy. *J. Med. Chem.* 39:1918–1020 (1996); Stahn, R., Schafer, H., Kernchen, F. and J. Schreiber. *Glycobiology* 8:311–319 (1998); Yamazaki, N., Jigami, Y., Gabius, H. -J., and S. Kojima. *Trends in Glycoscience and Glycotechnology* 13:319–329 (2001)). As above, systematic research into liposomes having a wide variety of sugar chains, on the glycolipids or glycoproteins bonded to the liposomes, including preparative methods and in vivo analyses thereof, is pending and represents an important challenge to be progressed in future.

Further, in research on new types of DDS materials, it is an important challenge to develop a DDS material capable of being orally administered in the easiest and cheapest way. For example, when a peptide medicine is orally administered, it is subject to enzymolysis and may be only partially absorbed in the intestine due to its water solubility, high molecular weight, and low permeability in the mucosa of small intestine. As an alternative, a ligand-bonded liposome is getting attention as a potential DDS material for delivering high molecular-weight medicines or genes into the blood stream through the intestine (Lehr, C. -M. *J. Controlled Release* 65:19–29 (2000)). However, results from research into an intestinal absorption-controlled liposome, using a sugar chain as the ligand, have not been reported.

SUMMARY OF THE INVENTION

It is therefore an object of the present invention to provide a sugar-modified liposome that is specifically recognized and bound by selected lectins (sugar-recognizing proteins) residing on the surface of target cells and tissues, and having excellent qualities of absorption, particularly in the intestine. It is a further object of the present invention to provide a liposome product comprising a drug or gene encapsulated by a sugar-modified liposome that is recognized by cells or tissues in vivo, and that can specifically deliver drugs or genes to target cells or tissues.

In order to meet the challenges mentioned above, various experimental tests and studies have been conducted on the properties of liposome surfaces, and on the sugar chains and linker proteins used to bond the sugar chains to the surface of liposomes. Through this research, it has been shown that the targeting performance of sugar-modified liposomes to particular target tissues can be controlled by the sugar chain structure. It has also been shown that the amount of liposome transferred to each target tissue can be increased by hydrating the liposome surface and/or the linker protein, resulting in more effective delivery of drugs or genes to each of the target cells or tissues.

According to a first aspect of the present invention, there is provided a liposome having a sugar chain bonded to the liposome membrane surface.

According to a second aspect of the present invention, there is provided a liposome having a sugar chain bonded to the liposome membrane surface, and further comprising tris (hydroxymethyl) aminomethane bonded to the liposome membrane surface.

According to a third aspect of the present invention, there is provided a liposome having a sugar chain bonded to the liposome membrane surface through a linker protein.

According to a fourth aspect of the present invention, there is provided a liposome having a sugar chain bonded to the liposome membrane surface through a linker protein, wherein both the liposome membrane surface and the linker protein are hydrophilized.

According to a fifth aspect of the present invention, there is provided a liposome product comprising the sugar-modified liposome according to any one of the first to fourth aspects of the present invention, and a drug or gene encapsulated in the sugar-modified liposome.

In each aspect of the present invention, the sugar chain is preferably selected from the group consisting of lactose disaccharide, 2'-fucosyllactose trisaccharide, difucosyllactose tetrasaccharide, 3-fucosyllactose trisaccharide, Lewis X trisaccharide, sialyl Lewis X tetrasaccharide, 3'-sialyllactosamine trisaccharide, and 6'-sialyllactosamine trisaccharide.

In each aspect of the present invention, preferably an adjusted amount of the sugar chain is bonded to the membrane surface of the liposome.

In each relevant aspect of the present invention, preferably the surface of the liposome and/or the linker protein is hydrophilized. Preferably, the hydrophilization is performed by using tris (hydroxymethyl) aminomethane.

In each relevant aspect of the present invention, the linker protein is preferably human serum albumin or bovine serum albumin.

DETAILED DESCRIPTION OF THE INVENTION

The present invention will now be described in detail.

A liposome generally means a closed vesicle consisting of a lipid layer formed as a membrane-like aggregation, and an inner water layer.

Figure 1:
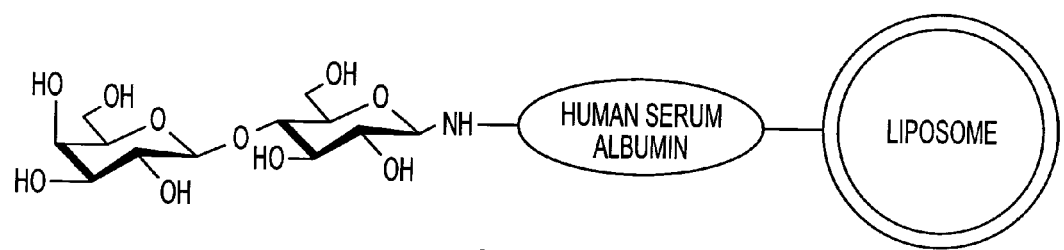
FIG. 1 is a schematic diagram of a liposome modified by lactose disaccharide.
Figure 2:
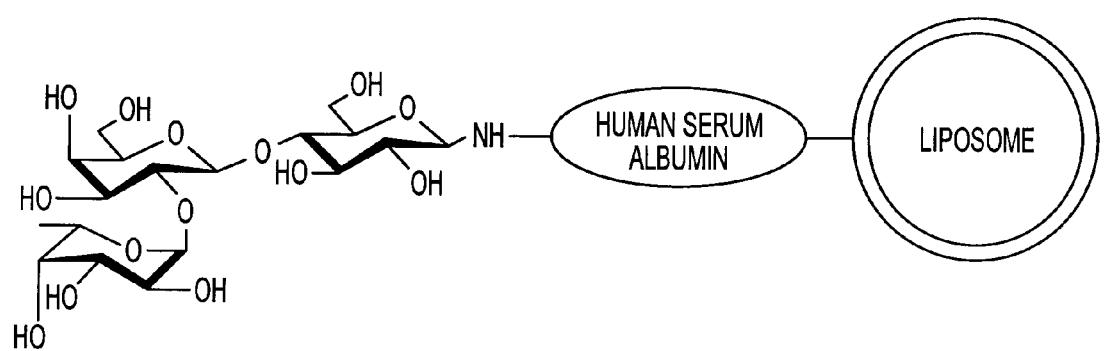
FIG. 2 is a schematic diagram of a liposome modified by 2'-fucosyllactose trisaccharide.
Figure 3:
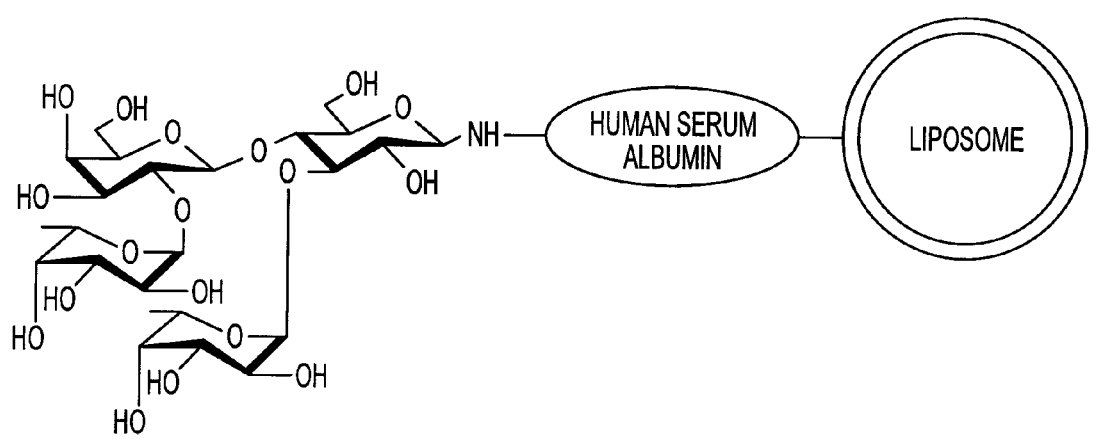
FIG. 3 is a schematic diagram of a liposome modified by difucosyllactose tetrasaccharide.
Figure 4:
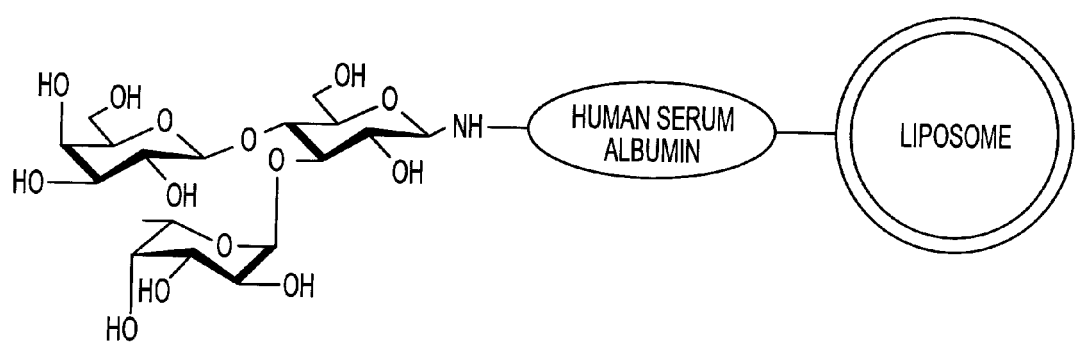
FIG. 4 is a schematic diagram of a liposome modified by 3-fucosyllactose trisaccharide.
Figure 5:
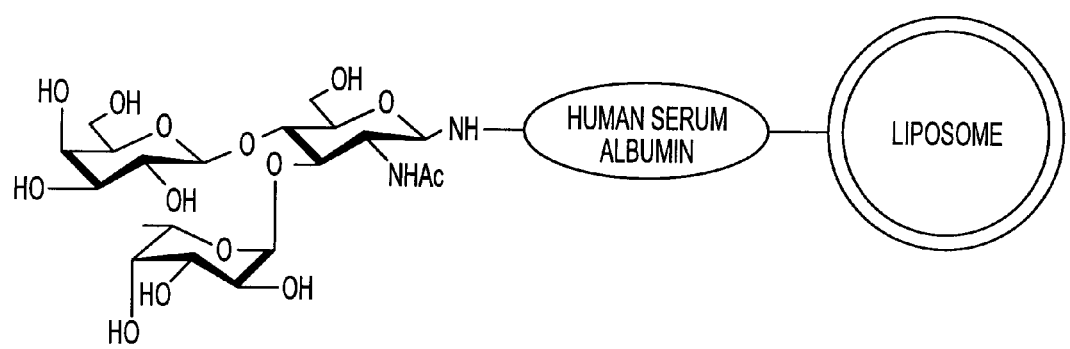
FIG. 5 is a schematic diagram of a liposome modified by Lewis X trisaccharide.
Figure 6:
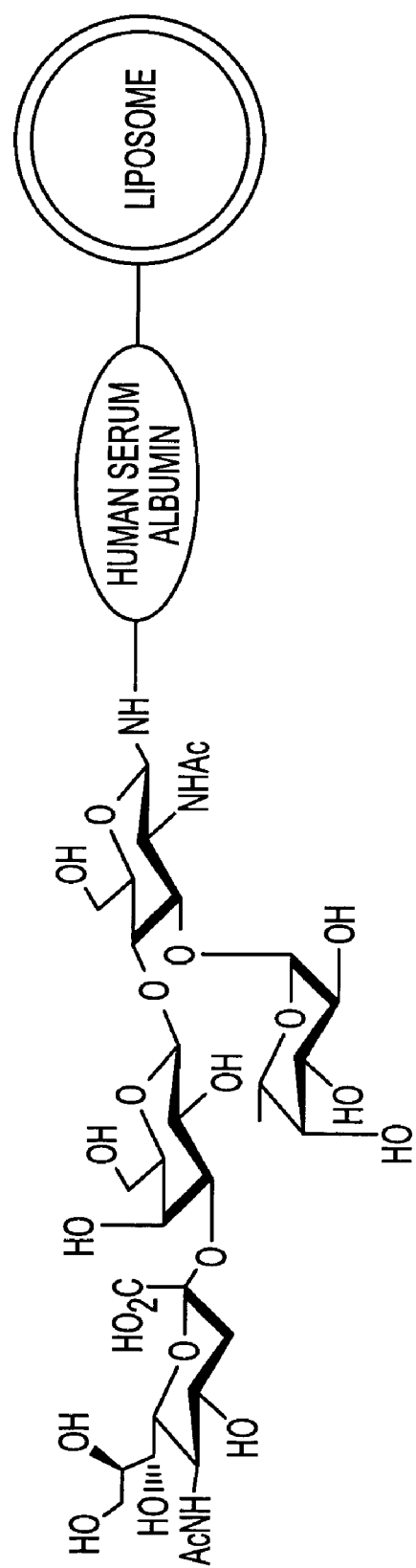
FIG. 6 is a schematic diagram of a liposome modified by sialyl Lewis X tetrasaccharide.
Figure 7:
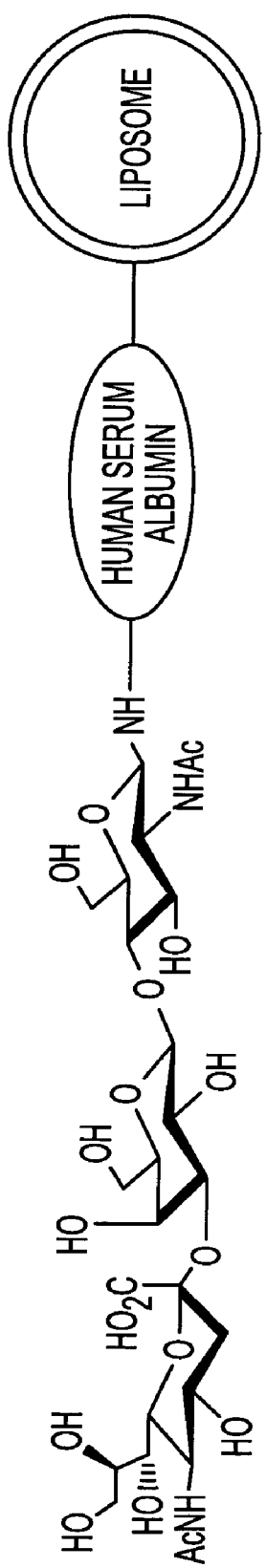
FIG. 7 is a schematic diagram of a liposome modified by 3'-sialyllactosamine trisaccharide.
Figure 8:
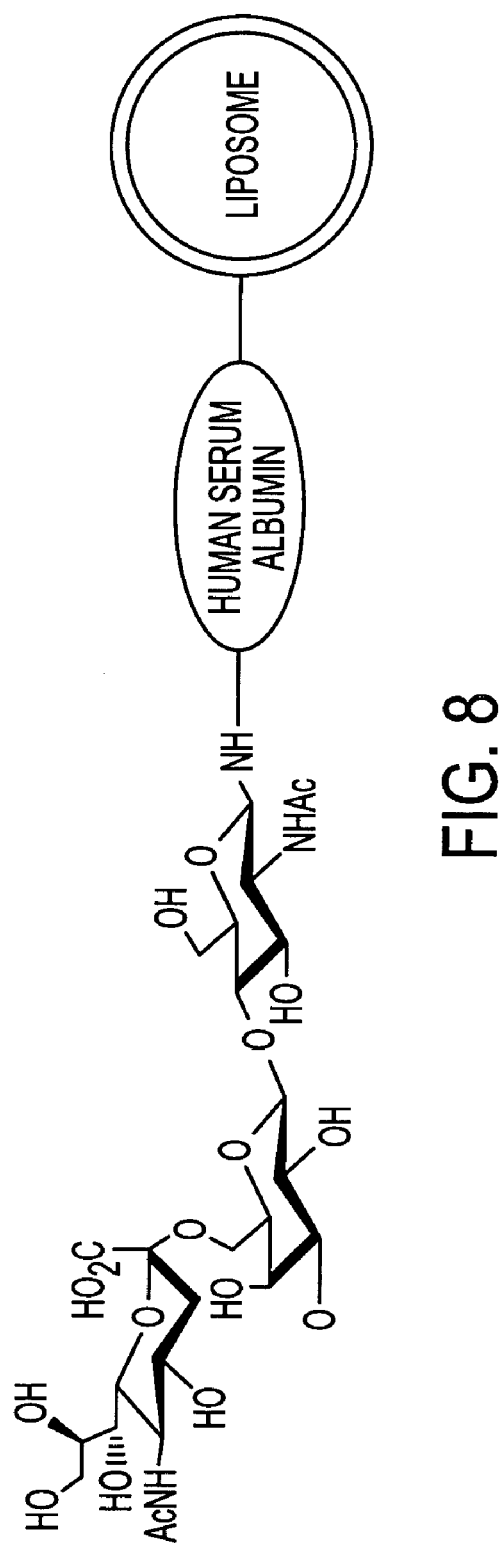
FIG. 8 is a schematic diagram of a liposome modified by 6'-sialyllactosamine trisaccharide.
Figure 9:
FIG. 9 is a schematic diagram of a liposome modified by tris (hydroxymethyl) aminomethane, as a comparative sample.
Figure 10:
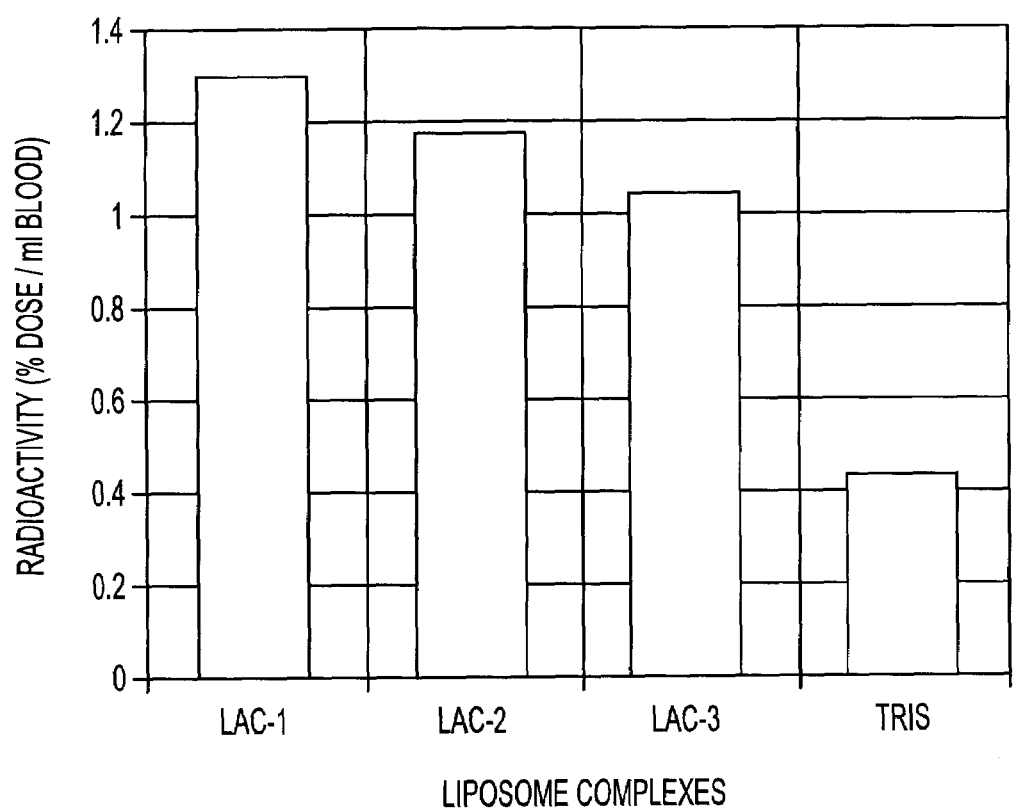
FIG. 10 is a diagram showing respective distribution rates in blood of 4 types of liposome complexes (including a TRIS comparative example), differing in the amount of lactose disaccharide bonded thereto, after 10 minutes from their intestinal administration.
Figure 11:
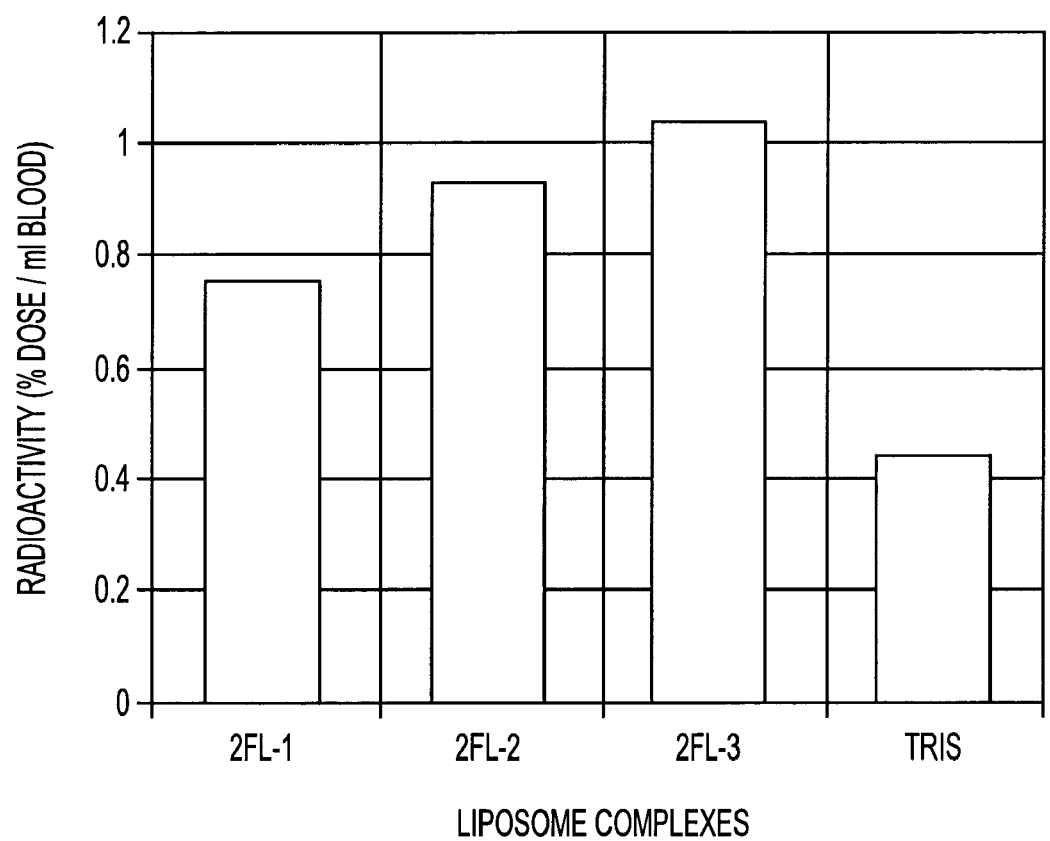
FIG. 11 is a diagram showing respective distribution rates in blood of 4 types of liposome complexes (including a TRIS comparative example), differing in the amount of 2'-fucosyllactose trisaccharide bonded thereto, after 10 minutes from their intestinal administration.
Figure 12:
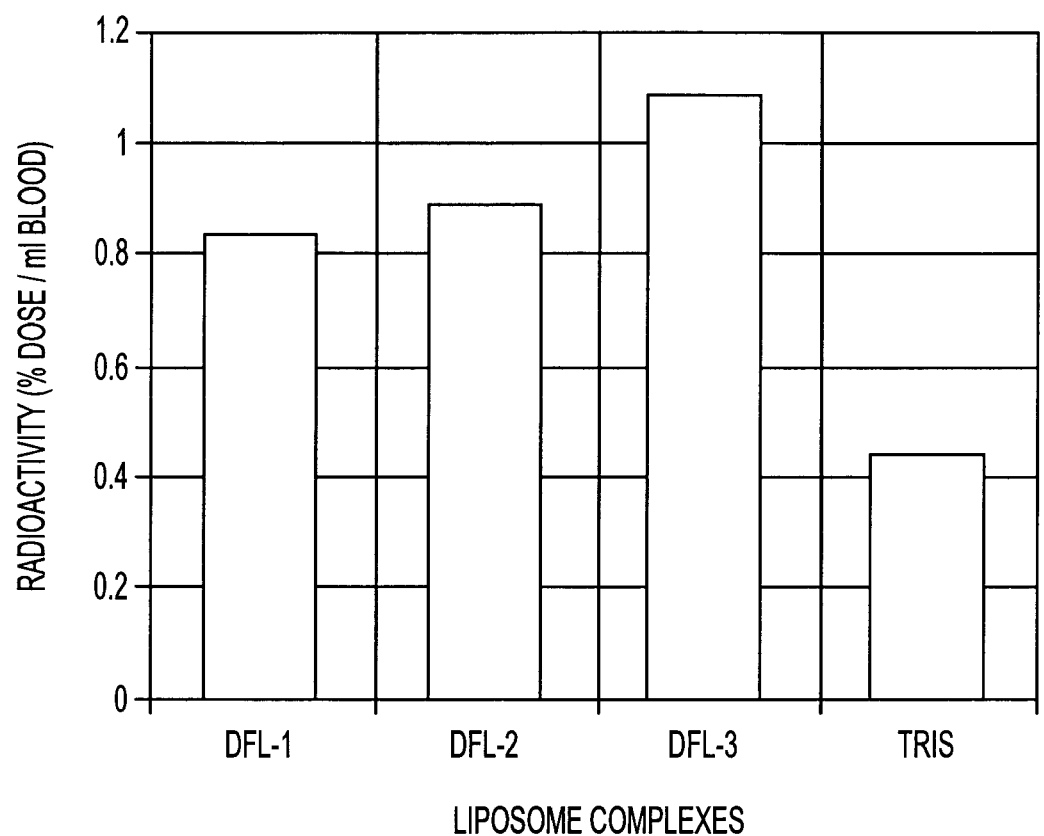
FIG. 12 is a diagram showing respective distribution rates in blood of 4 types of liposome complexes (including a TRIS comparative example), differing in the amount of difucosyllactose tetrasaccharide bonded thereto, after 10 minutes from their intestinal administration.
Figure 13:
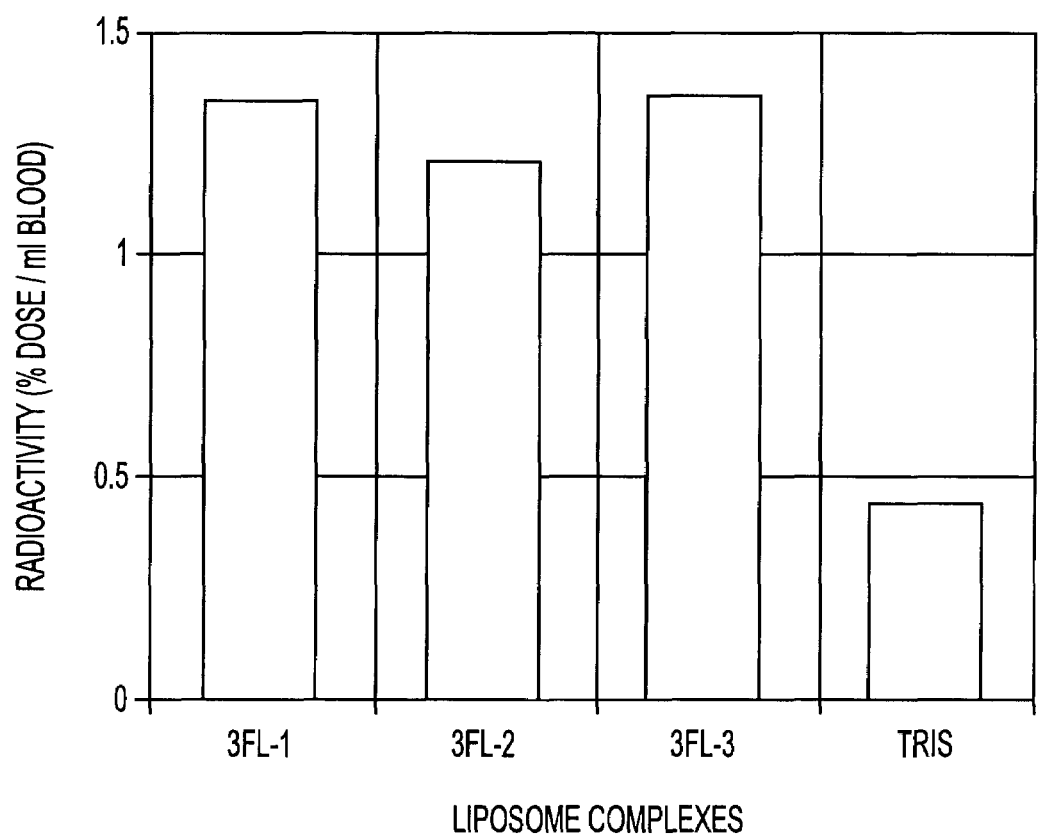
FIG. 13 is a diagram showing respective distribution rates in blood of 4 types of liposome complexes (including a TRIS comparative example), differing in the amount of 3-fucosyllactose trisaccharide bonded thereto, after 10 minutes from their intestinal administration.

As shown in FIGS. 1 to 8, a liposome of the present invention includes a liposome with a sugar chain covalently bonded to its membrane surface or its lipid layer through a linker protein such as human serum albumin. While only a single sugar chain-linker protein set, bonded to the liposome, is illustrated in FIGS. 1 to 8, these figures (including FIG. 9) are schematic diagrams, and a number of sugar chain-linker protein sets are actually bonded to the liposome surface.

The liposomes of the present invention are modified by a sugar chain. Preferred examples of the sugar chains include lactose disaccharide (Gal. beta. 1–4 Glc) shown in FIG. 1, 2'-fucosyllactose trisaccharide (Fuc. alpha.1–2 Gal. beta. 1–4 Glc) shown in FIG. 2, difucosyllactose tetrasaccharide (Fuc. alpha. 1–2 Gal. beta. 1–4 (Fuc. alpha. 1–3) Glc) shown in FIG. 3, 3-fucosyllactose trisaccharide (Gal. beta. 1–4(Fuc. alpha. 1–3) Glc) shown in FIG. 4, Lewis X trisaccharide (Gal. beta. 1–4 (Fuc. alpha. 1–3) GlcNAc) shown in FIG. 5, sialyl Lewis X tetrasaccharide (Neu5Ac. alpha. 2–3 Gal. beta. 1–4 (Fuc. alpha. 1–3) GlcNAc) shown in FIG. 6, 3'-sialyllacto trisaccharide (Neu5Ac. alpha. 2–3 Gal. beta. 1–4GlcNAc) shown in FIG. 7, and 6'-sialyllactosamine trisaccharide (Neu5Ac. alpha. 2–6 Gal. beta. 1–4 GlcNAc) shown in FIG. 8.

In the present invention, it is preferred to bond the sugar chain to the membrane surface of the liposome through a linker protein. Such liposome structures are shown in FIGS. 1 to 8, together with the chemical structures of the sugar chain.

The linker protein may be an animal serum albumin, such as human serum albumin (HSA) or bovine serum albumin (BSA). In particular, it has been verified through experimental tests using mice that a liposome complex using human serum albumin is taken into target tissues in a greater amount than a liposome complex using a different linker protein.

The lipid constituting the liposomes of the present invention includes phosphatidylcholines, phosphatidylethanolamines, phosphatidic acids, gangliosides, glycolipids, phosphatidylglycerols, and cholesterol. The phosphatidylcholines preferably include dimyristoylphosphatidylcholine, dipalmitoylphosphatidylcholine, and distearoylphosphatidylcholine. The phosphatidylethanolamines preferably include dimyristoylphosphatidylethanolamine, dipalmitoylphosphatidylethanolamine, and distearoylphosphatidylethanolamine. The phosphatidic acids preferably include dimyristoylphosphatidic acid, dipalmitoylphosphatidic acid, distearoylphosphatidic acid, and dicetylphosphoric acid. The gangliosides preferably include ganglioside GM1, ganglioside GD1a, and ganglioside GT1b. The glycolipids preferably include galactosylceramide, glucosylceramide, lactosylceramide, phosphatide, and globoside. The phosphatidylglycerols preferably include dimyristoylphosphatidylglycerol, dipalmitoylphosphatidylglycerol, and distearoylphosphatidylglycerol.

While a regular liposome may be used in the invention, it is preferable to hydrophilize the surface of the liposome.

The liposome itself can be produced through any conventional method including a thin film method, a reverse phase evaporation method, an ethanol injection method, and a dehydration-rehydration method.

The particle size of the liposome can be controlled through an ultrasonic radiation method, an extrusion method, a French press method, a homogenization method or any other suitable conventional method.

A specific method of producing the liposome itself of the present invention will be described below. For example, a mixed micelle is first prepared by mixing a compounded lipid consisting of phosphatidylcholines, cholesterol, phosphatidylethanolamines, phosphatidic acids, and gangliosides or glycolipids or phosphatidylglycerols, with sodium cholic acid serving as a surfactant. Particularly, the phosphatidylethanolamines are essentially compounded to provide a hydrophilic reaction site, and the composition of gangliosides or glycolipids or phosphatidylglycerols are essentially compounded to provide a bonding site for the linker protein.

The obtained mixed micelle is subjected to ultrafiltration to prepare a liposome. Then, the membrane surface of the liposome is hydrophilized by applying a bivalent crosslinking reagent and tris (hydroxymethyl) aminomethane onto the lipid phosphatidylethanolamine of the membrane of the liposome.

The liposome can be hydrophilized through a conventional method such as a method of producing a liposome by using phospholipids covalently bonded with polyethylene glycol, polyvinyl alcohol, maleic anhydride copolymer or the like (Japanese Patent Laid-Open Publication No. 2001-302686). However, in the present invention, it is particularly preferable to hydrophilize the liposome membrane surface by using tris (hydroxymethyl) aminomethane.

The technique using tris (hydroxymethyl) aminomethane has some advantages superior to the conventional method of using polyethylene glycol or the like. For example, when a sugar chain is bonded onto a liposome and the molecular recognition function of the sugar chain is utilized for bringing about the targeting performance as in the present invention, the tris (hydroxymethyl) aminomethane is particularly preferable because it is a substance having a low molecular weight. More specifically, as compared to the conventional method using a substance having a high molecular weight such as polyethylene glycol, the tris (hydroxymethyl) aminomethane is less apt to become a three-dimensional obstacle to the sugar chain and to prevent the lectin (sugar-recognizing protein) on the membrane surface of target cells from recognizing the sugar-chain molecule.

In addition, the liposome according to the present invention is excellent in terms of particle-size distribution, composition, and dispersing characteristics, as well as in long-term storage stability and in vivo stability, even after the above hydrophilization, and thereby is suitable for forming into and using as a liposome product.

As an example of the process for forming of a liposome hydrophilized through the use of tris (hydroxymethyl) aminomethane, a bivalent reagent is added to a liposome solution. Exemplary bivalent reagents include bissulfosuccinimidylsuberate, disuccinimidylglutarate, dithiobissuccinimidylpropionate, disuccinimidylsuberate, 3,3'-dithiobissulfosuccinimidylpropionate, ethylene glycol bissuccinimidylsuccinate, or ethylene glycol bissulfosuccinimidylsuccinate. Exemplary lipids include dimyristoylphosphatidylethanolamine, dipalmitoylphosphatidylethanolamine, and distearoylphosphatidylethanolamine. Upon combination, a reaction between the bivalent reagent and the lipid occurs so as to bond the bivalent reagent to the lipid on the membrane of the liposome. Then, the tris (hydroxymethyl) aminomethane is reacted with the bivalent reagent to bond the tris (hydroxymethyl) aminomethane to the liposome surface.

In the present invention, the sugar chain may be bonded to the liposome through a linker protein. The linker protein is first bonded to the liposome by first treating the liposome with an oxidant such as $NaIO_4$, $Pb(O_2CCH_3)_4$, or $NaBiO_3$ to oxidize the gangliosides residing on the membrane surface of the liposome. The linker protein is then bonded to the gangliosides on the liposome membrane surface by a reductive amination reaction using a reagent such as $NaBH_3CN$ or $NaBH_4$.

Preferably, the linker protein is also hydrophilized by bonding a moiety having a hydroxy group to the linker protein. For example, tris (hydroxymethyl) aminomethane may be bonded to the linker protein on the liposome by using a bivalent reagent such as bissulfosuccinimidylsuberate, disuccinimidylglutarate, dithiobissuccinimidylpropionate, disuccinimidylsuberate, 3,3'-dithiobissulfosuccinimidylpropionate, ethylene glycol bissuccinimidylsuccinate, or ethylene glycol bissulfosuccinimidylsuccinate, as discussed above.

One of the ends of a bivalent crosslinking reagent is bonded to the amino groups of the linker protein. Then, the reduction terminals of desired types of sugar chains are glycosylaminated to prepare a sugar-chain glycosylamine compound, and the amino groups of the obtained sugar chains are bonded to a part of the other unreacted ends of the bivalent crosslinking reagent bonded to the linker protein on the liposome.

Then, the surface of the resulting linker protein which resides on the membrane surface of the liposome has the sugar chain bonded thereto and is hydrophilized by using the mostly remaining unreacted ends of the bivalent reagent to which no sugar chain is bonded. That is, a bonding reaction is caused between the unreacted ends of the bivalent reagent bonded to the linker protein on the liposome and tris (hydroxymethyl) aminomethane, so as to hydrophilize the liposome surface to obtain the liposome according to the present invention.

The hydrophilization of the liposome surface and the linker protein provides enhanced mobility toward various tissues and enhanced sustainability in various tissues. This advantage is realized because the hydrophilized liposome surface and linker protein become hydrated by water molecules in vivo or in a blood vessel, which allows a portion of the liposome complex, other than the sugar chain, to function as if it is a layer of water which is not recognized by the various tissues. The liposome complex is thus not recognized by any tissues other than target tissues and only through the sugar chain is recognized by the lectin (sugar-recognizing protein) of the target tissues.

As a next general step in the production of the sugar-modified liposomes of the present invention, the sugar chain is bonded to the linker protein on the liposome. For this purpose, the reduction terminal of the sugars constituting the sugar chain is, for example, glycosylaminated by using ammonium salts such as $NH_4HCO_3$ or $NH_2COONH_4$, and then the linker protein bonded onto the liposome membrane surface is bonded to the above glycosylaminated sugars using a bivalent reagent such as bissulfosuccinimidylsuberate, disuccinimidylglutarate, dithiobissuccinimidylpropionate, disuccinimidylsuberate, 3,3'-dithiobissulfosuccinimidylpropionate, ethylene glycol bissuccinimidylsuccinate, or ethylene glycol bissulfosuccinimidylsuccinate to obtain the liposomes shown in FIGS. 1–8.

The sugar-modified liposomes of the present invention generally exhibit significantly high intestinal absorption. In addition, the intestinal absorption of the liposomes can be controlled by adjusting the density of the sugar chains bonded to the liposome, so that the liposome can more efficiently deliver drugs to target regions with reduced side effects. For example, FIGS. 10 to 13 show the results of studies performed to determine the rates of distribution (or intestinal absorption) of four different sugar-modified liposomes from intestine to blood, where the amount of sugar chain bonded to the respective liposomes is changed in three levels.

In these experiments, the amount of sugar chain bonded to the respective liposomes is changed by bonding the sugar chain to the linker protein-bonded liposome at three density levels: (1) 50 μg, (2) 200 μg, and (3) 1 mg. As shown in the Figures, when lactose disaccharide is used as the sugar chain, the intestinal absorption is gradually lowered as the density of the sugar chain is increased. By contrast, when 2'-fucosyllactose trisaccharide or difucosyllactose tetrasaccharide is used as the sugar chain, the intestinal absorption is increased as the density of the sugar chain is increased. When 3-fucosyllactose trisaccharide is used as the sugar chain, the intestinal absorption is lowered and then increased as the density of the sugar chain is increased.

These characteristics show that intestinal absorption is altered by the amount of sugar chain bonded to the liposome for each type of sugar chain. Thus, intestinal absorption can be controlled by appropriately selecting the amount and type of sugar chain bonded to the liposome.

The results from additional experiments demonstrate that the type and amount of sugar chain bonded to the surface of the sugar-modified liposomes of the present invention can directly effect the targeting performance of the liposomes to particular target cells or tissues. The results of these experiments are shown in FIGS. 14 to 21.

Figure 14:
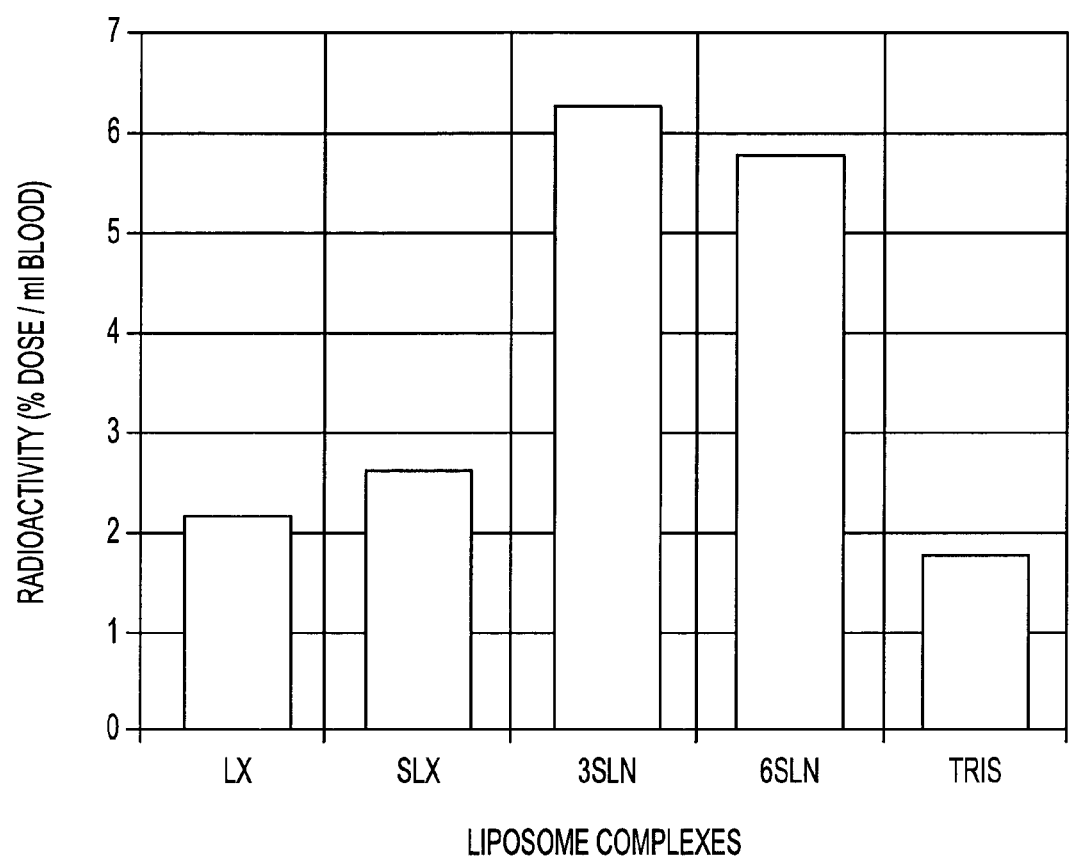
FIG. 14 is a diagram showing respective distribution rates in blood of 5 types of liposome (including a TRIS comparative example) complexes after 60 minutes from their intravenous administration.
Figure 15:
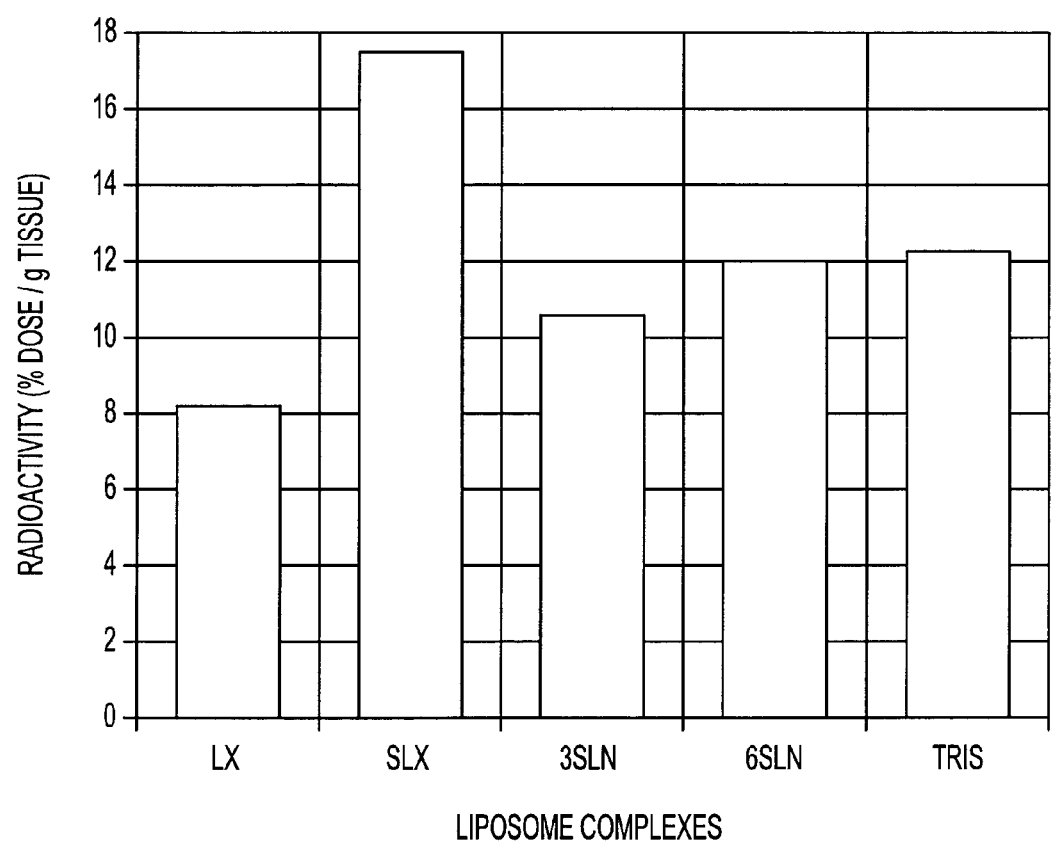
FIG. 15 is a diagram showing respective distribution rates in liver of 5 types of liposome complexes (including a TRIS comparative example) after 60 minutes from their intravenous administration.
Figure 16:
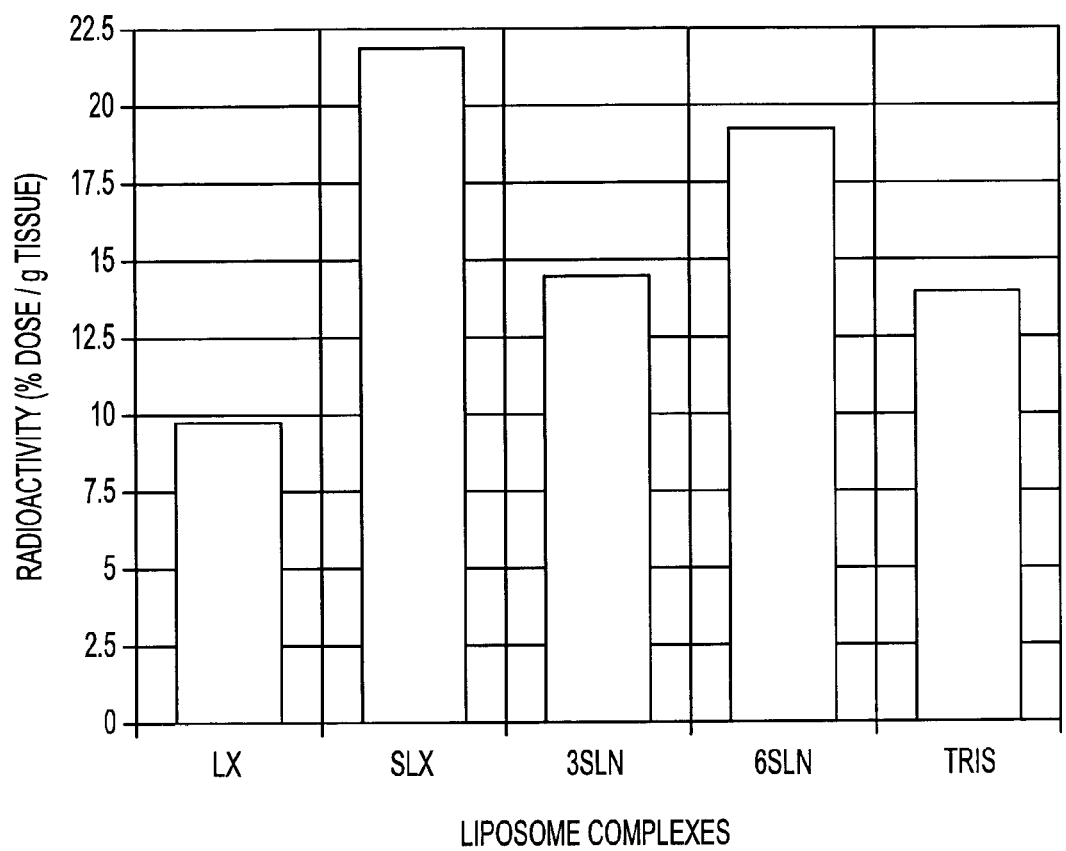
FIG. 16 is a diagram showing respective distribution rates in spleen of 5 types of liposome complexes (including a TRIS comparative example) after 60 minutes from their intravenous administration.
Figure 17:
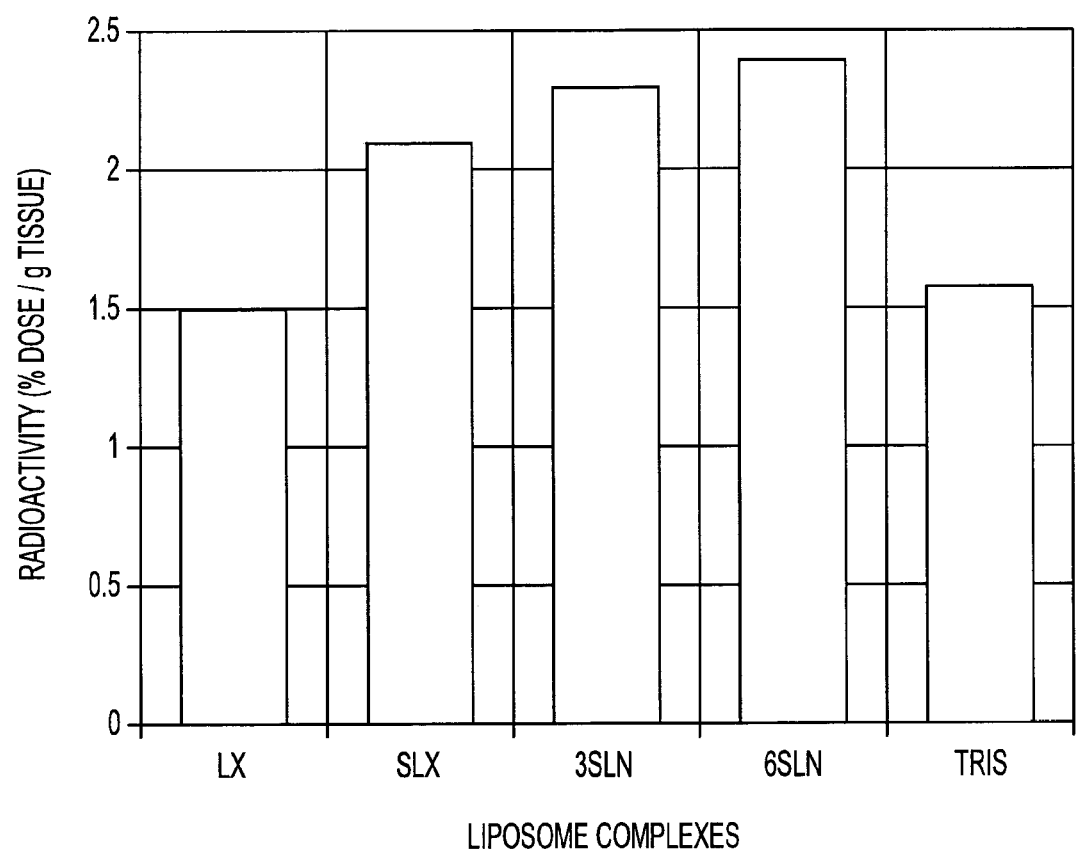
FIG. 17 is a diagram showing respective distribution rates in lung of 5 types of liposome complexes (including a TRIS comparative example) after 60 minutes from their intravenous administration.
Figure 18:
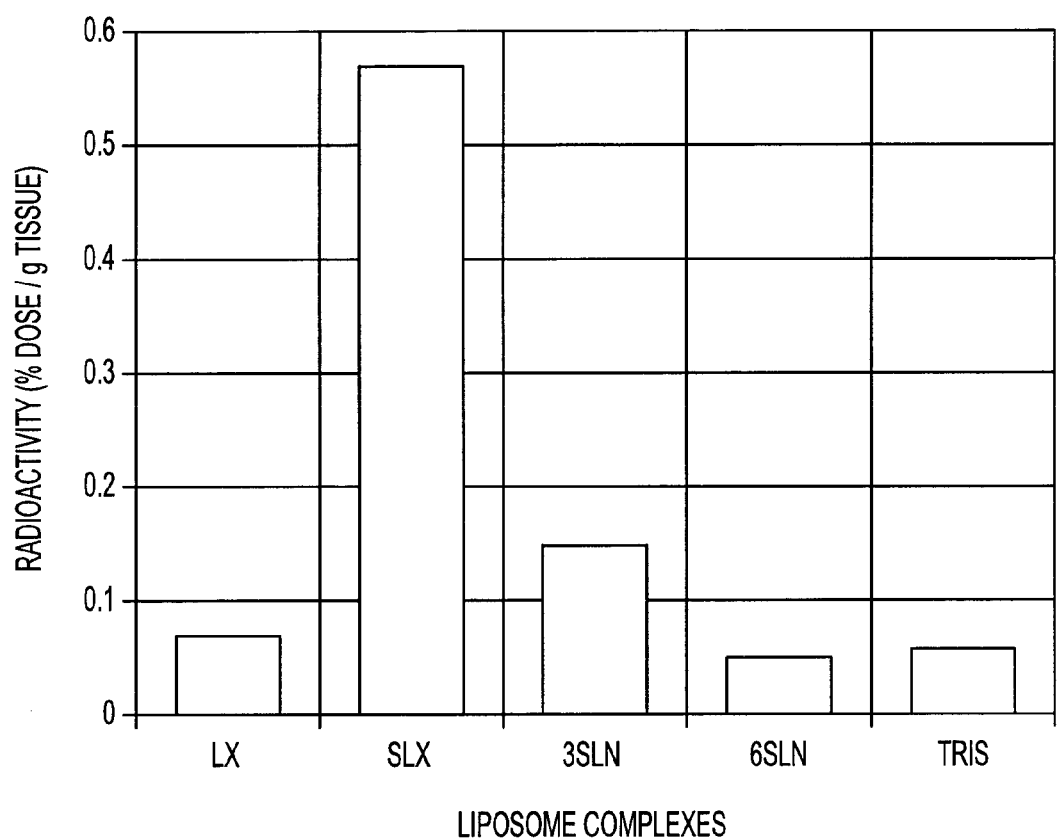
FIG. 18 is a diagram showing respective distribution rates in brain of 5 types of liposome complexes (including a TRIS comparative example) after 60 minutes from their intravenous administration.
Figure 19:
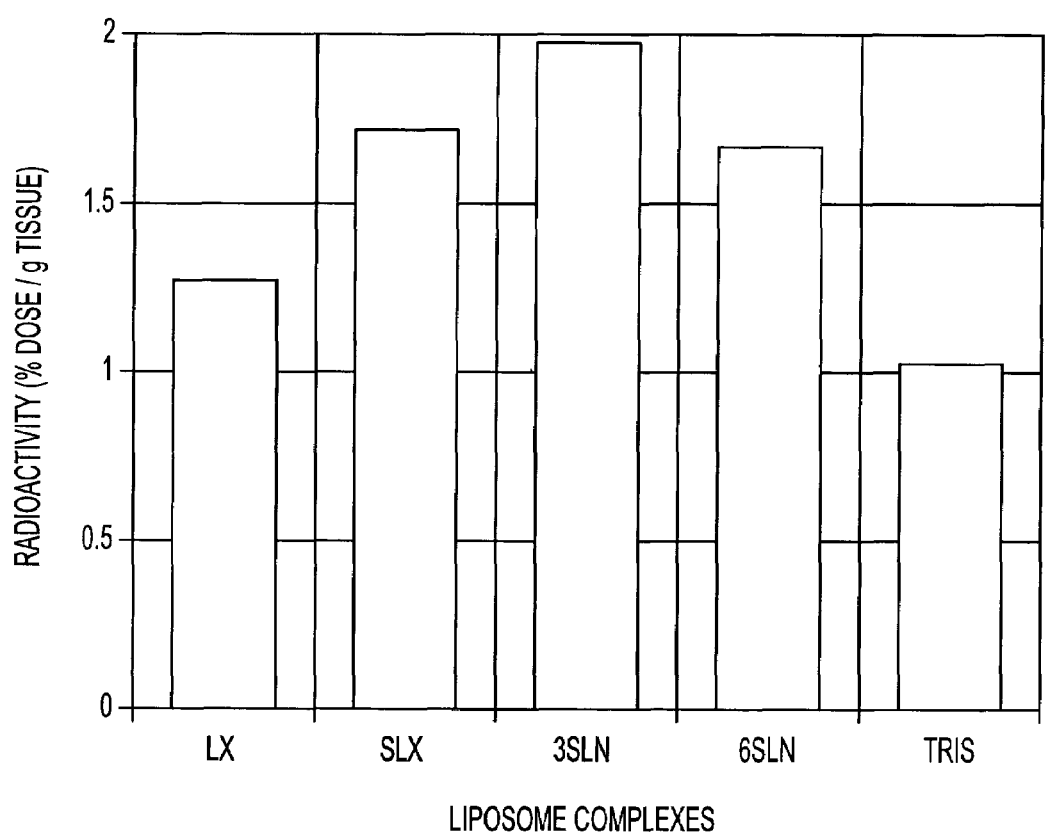
FIG. 19 is a diagram showing respective distribution rates in cancer tissues of 5 types of liposome complexes (including a TRIS comparative example) after 60 minutes from their intravenous administration.
Figure 20:
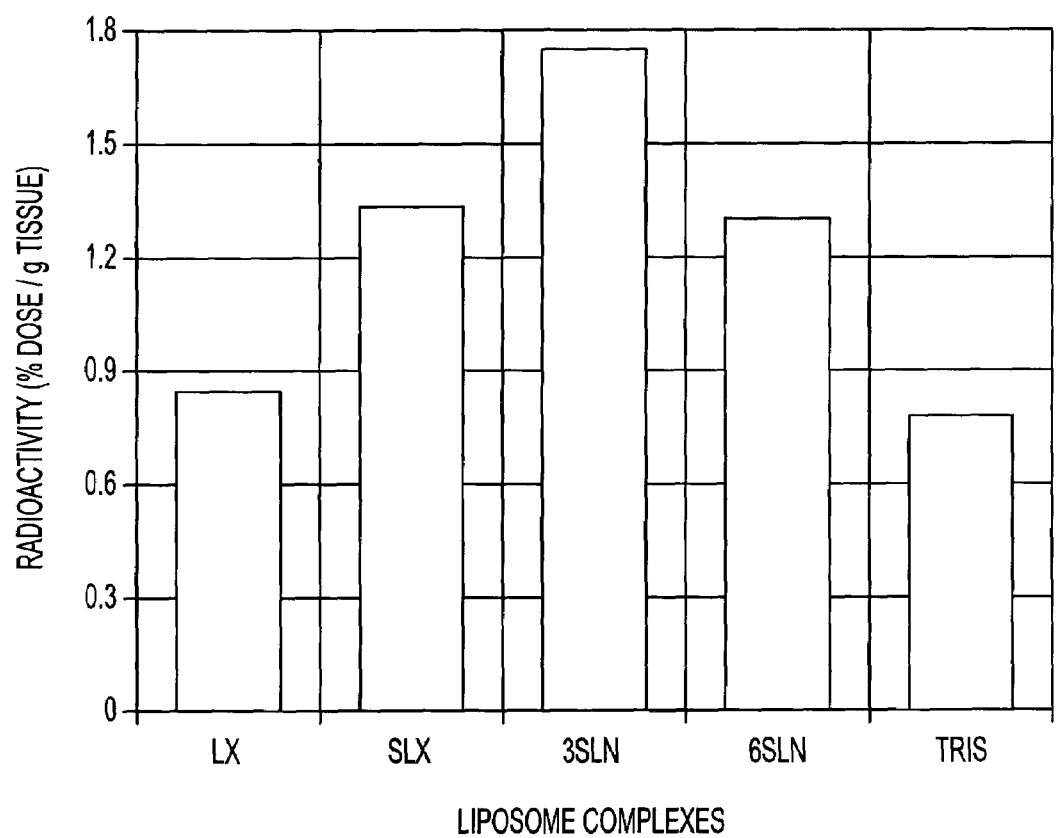
FIG. 20 is a diagram showing respective distribution rates in inflammatory tissues of 5 types of liposome complexes (including a TRIS comparative example) after 60 minutes from their intravenous administrations.
Figure 21:
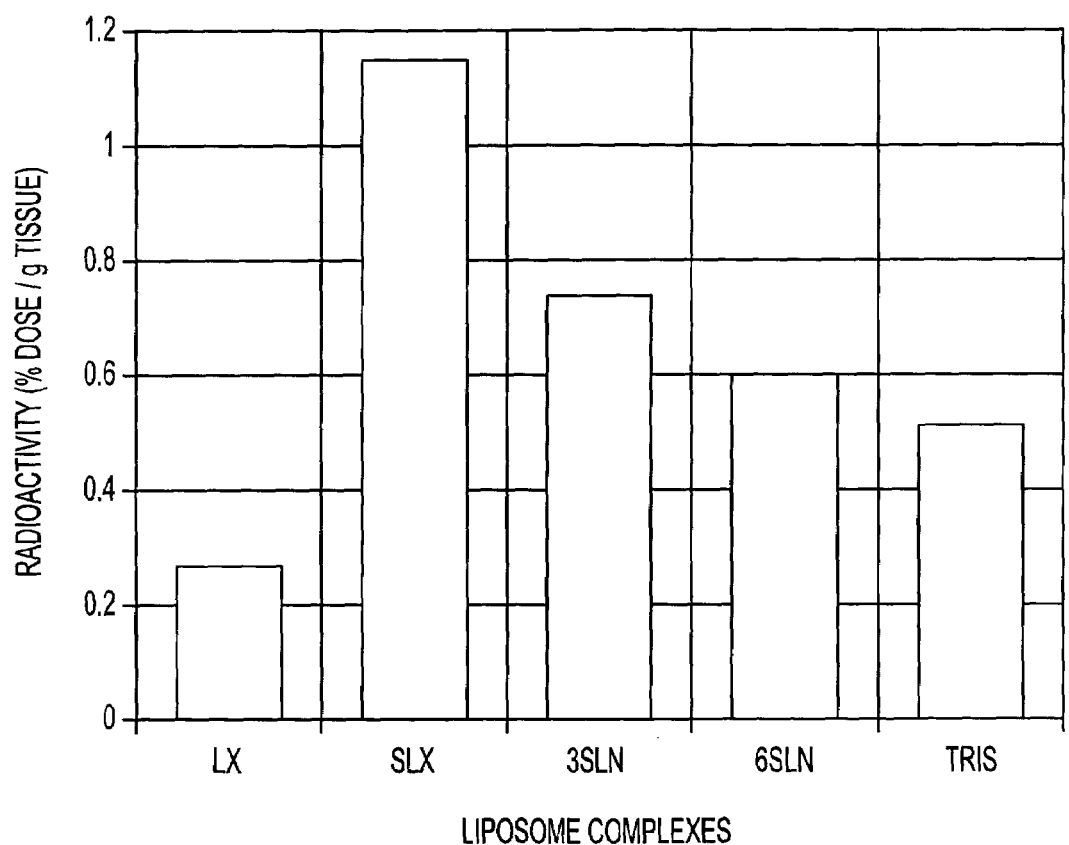
FIG. 21 is a diagram showing respective distribution rates in lymph node of 5 types of liposome complexes (including a TRIS comparative example) after 60 minutes from their intravenous administration.

For example, it is evident from the results that liposomes (LX, SLX, 3SLN, 6SLN) modified by four types of sugar chains: Lewis X trisaccharide, sialyl Lewis X tetrasaccharide, 3'-sialyllactosamine trisaccharide, and 6'-sialyllactosamine trisaccharide, generally have a high targeting performance to cancer tissues and inflammatory tissues (FIGS. 19 and 20). In particular, sialyl Lewis X tetrasaccharide modified liposomes (SLX) have a high targeting performance to liver, spleen, brain and lymph node (FIGS. 15, 16, 18 and 21), 3'-sialyllactosamine trisaccharide modified liposomes (3SLN) have a high targeting performance to blood, brain and cancer tissues (FIGS. 14, 18, and 19), and 6'-sialyllactosamine trisaccharide modified liposomes (6SLN) have a high targeting performance to blood and lung (FIG. 14 and 17).

The liposome product obtained by encapsulating drugs or genes for therapeutic or diagnostic purposes, using the sugar-modified liposomes of the present invention, would also have a targeting performance selectively controlled by the amount and identity of the sugar chains bonded to the liposome. Thus, the liposome product of the present invention can be used to provide enhanced delivery of therapeutic drugs or diagnostic agents to target cells and tissues, as well as to suppress side effects by reducing the ability of drugs to be taken into non-target cells and tissues.

Drugs, such as cancer drugs, or genes, such as those used in gene therapy, may be encapsulated in the sugar-modified liposomes of the present invention through any suitable conventional method including a method of forming the liposome by using a solution including the drugs or genes, and a lipid such as a phosphatidylcholines or phosphatidylethanolamines.

Various examples of the present invention will be described below, but the invention is not limited thereto.

EXAMPLE 1

Preparation of Liposomes

Liposomes were prepared through an improved type of cholate dialysis based on a previously reported method (Yamazaki, N., Kodama, M. and H. -J. Gabius. *Methods Enzymol.* 242:56–65 (1994)). More specifically, 46.9 mg of sodium cholate was added to 45.6 mg of lipid mixture consisting of dipalmitoylphosphatidylcholine, cholesterol, dicetylphosphate, ganglioside and dipalmitoylphosphatidylethanolamine at a mole ratio of 35:40:5:15:5, respectively, and the lipid mixture was dissolved in 3 ml of chloroform/methanol solution. The solution was then evaporated, and the resulting deposit was dried in vacuo to obtain a lipid membrane. The obtained lipid membrane was suspended in 3 ml of a TAPS buffer solution (pH 8.4), and was subjected to a supersonic treatment to obtain a clear micelle suspension. Then, this micelle suspension was subjected to ultrafiltration by using a PM 10 membrane (Amicon Co., USA) and a PBS buffer solution (pH 7.2) to prepare 10 ml of a uniform liposome (average size of 100 nm).

EXAMPLE 2

Hydrophilization of Lipid Membrane Surface of Liposomes 10 ml of the liposome solution prepared in Example 1 was subjected to ultrafiltration by using an XM 300 membrane (Amicon Co., USA) and a CBS buffer solution (pH 8.5) to adjust the pH of the solution to 8.5. Then, 10 mg of bis (sulfosuccinimidyl) suberate (BS3; Pierce Co., USA) crosslinking reagent was added to the liposome solution. The obtained solution was stirred at 25° C. for 2 hours, and subsequently stirred at 7° C. for one night to complete the reaction between the BS3 and the dipalmitoylphosphatidyletanolamine of the lipid on the liposome membrane. This liposome solution was then subjected to ultrafiltration by using an XM 300 membrane and a CBS buffer solution (pH 8.5). Then, 40 mg of tris (hydroxymethyl) aminomethane dissolved in 1 ml of CMS buffer solution (pH 8.5) was added to 10 ml of the liposome solution. The obtained solution was stirred at 25° C. for 2 hours, and stirred at 7° C. for one night to complete the reaction between the BS3 bonded to the lipid on the liposome membrane and the tris (hydroxymethyl) aminomethane. In this manner, the hydroxyl groups of the tris (hydroxymethyl) aminomethane were coordinated on the dipalmitoylphosphatidyletanolamine of the lipid on the liposome membrane to achieve the hydrophilization of the lipid membrane surface of the liposome.

EXAMPLE 3

Bonding of Human Serum Albumin (HSA) to Membrane Surface of Liposomes

Human serum albumin (HSA) was bonded to the membrane surface of the liposome through a coupling reaction method based on a previously reported method (Yamazaki, N., Kodama, M. and H. -J. Gabius. *Methods Enzymol.* 242:56–65 (1994)). More specifically, the reaction was carried out through a two-stage reaction method. That is, 43 mg of sodium metaperiodate dissolved in 1 ml of TAPS buffer solution (pH 8.4) was added to 10 ml of the liposome obtained in Example 2, and the obtained solution was stirred at room temperature for 2 hours to periodate-oxidize the ganglioside on the membrane surface of the liposome. Then, the solution was subjected to ultrafiltration by using an XM 300 membrane and a PBS buffer solution (pH 8.0) to obtain 10 ml of oxidized liposome. 20 mg of human serum albumin (HSA) was then added to the liposome solution, and the obtained solution was stirred at 25° C. for 2 hours. Then, 100 μl of 2M NaBH$_3$CN was added to the PBS buffer solution (pH 8.0), and the obtained solution was stirred at 10° C. for one night to bond the HSA to the liposome membrane surface through a coupling reaction between the HSA and the ganglioside on the liposome. Then, 10 ml of HSA-bonded liposome solution was obtained through an ultrafiltration using an XM 300 membrane and a CBS buffer solution (pH 8.5).

EXAMPLE 4

Bonding of Lactose Disaccharide to Human Serum Albumin (HSA) Bonded on Liposome Membrane Surfaces 50 μg, 200 μg, or 1 mg of lactose disaccharide (Wako Pure Chemical Co., Japan) was added to 0.5 ml of water solution having 0.25 g of NH$_4$HCO$_3$ dissolved therein, and the obtained solution was stirred at 37° C. for 3 days. Then, the solution was filtered by using a filter of 0.45 μm to complete an amination reaction at the reduction terminal of the sugar chain and obtain 50 μg of glycosylamine compound of the lactose disaccharide. Then, 1 mg of 3,3'-dithiobis (sulfosuccinimidyl propionate) (DTSSP; Pierce Co., USA) serving as a crosslinking reagent was added to 1 ml of a part of the liposome solution obtained in Example 3. The obtained solution was then stirred at 25° C. for 2 hours, and subsequently stirred at 7° C. for one night. Then, the solution was subjected to ultrafiltration by using an XM 300 membrane and a CBS buffer solution (pH 8.5) to obtain 1 ml of liposome in which the DTSSP was bonded to the HSA on the liposome. Then, 50 μg of the glycosylamine compound of the lactose disaccharide was added to the liposome solution. The obtained solution was stirred at 25° C. for 2 hours, and subsequently stirred at 7° C. for one night. Then, the solution was subjected to ultrafiltration by using an XM 300 membrane and a PBS buffer solution (pH 7.2) to bond the lactose disaccharide to the DTSSP on the human serum albumin bonded on the liposome membrane surface. In this manner, 3 types of liposomes (2 ml each), differing in the amount of sugar chain bonded thereto (referred to as LAC-1 (50 μg), LAC-2 (200 μg), and LAC-3 (1 mg)), in which lactose disaccharide is bonded to the liposome through human serum albumin (FIG. 1) (total lipid mass: 2 mg, total protein mass: 200 μg, average particle size: 100 nm), were obtained.

EXAMPLE 5

Bonding of 2'-Fucosyllactose Trisaccharide to Human Serum Albumin (HSA) Bonded on Liposome Membrane Surfaces 50 μg, 200 μg, or 1 mg of 2'-fucosyllactose trisaccharide (Wako Pure Chemical Co., Japan) was added to 0.5 ml of water solution having 0.25 g of NH$_4$HCO$_3$ dissolved therein, and the obtained solution was stirred at 37° C. for 3 days. The solution was then filtered by using a filter of 0.45 μm to complete an amination reaction at the reduction terminal of the sugar chain and obtain 50 μg of glycosylamine compound of the 2'-fucosyllactose trisaccharide. Then, 1 mg of 3,3'-dithiobis(sulfosuccinimidyl propionate) (DTSSP; Pierce Co., USA) serving as a crosslinking reagent was added to 1 ml of a part of the liposome solution obtained in Example 3. The obtained solution was stirred at 25° C. for 2 hours, and subsequently stirred at 7° C. for one night. Then, the solution was subjected to ultrafiltration by using an XM 300 membrane and a CBS buffer solution (pH 8.5) to obtain 1 ml of liposome in which the DTSSP was bonded to the HSA on the liposome. Then, 50 μg of the glycosylamine compound of the 2'-fucosyllactose trisaccharide was added to the liposome solution. The obtained solution was stirred at 25° C. for 2 hours, and subsequently stirred at 7° C. for one night. Then, the solution was subjected to ultrafiltration by using an XM 300 membrane and a PBS buffer solution (pH 7.2) to bond the 2'-fucosyllactose trisaccharide to the DTSSP on the human serum albumin bonded on the liposome membrane surface. In this manner, 3 types of liposomes (2 ml each), differing in the amount of sugar chain bonded thereto (referred to as 2FL-1 (50 μg), 2FL-2 (200 μg), and 2FL-3 (1 mg)), in which 2'-fucosyllactose trisaccharide is bonded to the liposome through human serum albumin (FIG. 2) (total lipid mass: 2 mg, total protein mass: 200 μg, average particle size: 100 nm), were obtained.

EXAMPLE 6

Bonding of Difucosyllactose Tetrasaccharide to Human Serum Albumin (HSA) Bonded on Liposome Membrane Surfaces 50 μg, 200 μg, or 1 mg of difucosyllactose tetrasaccharide (Wako Pure Chemical Co., Japan) was added to 0.5 ml of water solution having 0.25 g of $NH_4HCO_3$ dissolved therein, and the obtained solution was stirred at 37° C. for 3 days. The solution was then filtered by using a filter of 0.45 μm to complete an amination reaction at the reduction terminal of the sugar chain to obtain 50 μg of glycosylamine compound of the difucosyllactose tetrasaccharide. Then, 1 mg of 3,3'-dithiobis(sulfosuccinimidyl propionate) (DTSSP; Pierce Co., USA) serving as a crosslinking reagent was added to 1 ml of a part of the liposome solution obtained in Example 3. The obtained solution was stirred at 25° C. for 2 hours, and subsequently stirred at 7° C. for one night. Then, the solution was subjected to ultrafiltration by using an XM 300 membrane and a CBS buffer solution (pH 8.5) to obtain 1 ml of liposome in which the DTSSP was bonded to the HSA on the liposome. Then, 50 μg of the glycosylamine compound of the difucosyllactose tetrasaccharide was added to the liposome solution. The obtained solution was stirred at 25° C. for 2 hours, and subsequently stirred at 7° C. for one night. Then, the solution was subjected to ultrafiltration by using an XM 300 membrane and a PBS buffer solution (pH 7.2) to bond the difucosyllactose tetrasaccharide to the DTSSP on the human serum albumin bonded on the liposome membrane surface. In this manner, 3 types of liposomes (2 ml each), differing in the amount of sugar chain bonded thereto (referred to as DFL-1 (50 μg), DFL-2 (200 μg), and DFL-3 (1 mg)), in which difucosyllactose tetrasaccharide is bonded to the liposome through human serum albumin (FIG. 3) (total lipid mass: 2 mg, total protein mass: 200 μg, average particle size: 100 nm), were obtained.

EXAMPLE 7

Bonding of 3-Fucosyllactose Trisaccharide to Human Serum Albumin (HSA) Bonded on Liposome Membrane Surfaces 50 μg, 200 μg, or 1 mg of 3-fucosyllactose trisaccharide (Wako Pure Chemical Co., Japan) was added to 0.5 ml of water solution having 0.25 g of $NH_4HCO_3$ dissolved therein, and the obtained solution was stirred at 37° C. for 3 days. The solution was then filtered by using a filter of 0.45 μm to complete an amination reaction at the reduction terminal of the sugar chain to obtain 50 μg of glycosylamine compound of 3-fucosyllactose' trisaccharide. Then, 1 mg of 3,3'-dithiobis (sulfosuccinimidyl propionate) (DTSSP; Pierce Co., USA) serving as a crosslinking reagent was added to 1 ml of a part of the liposome solution obtained in Example 3. The obtained solution was stirred at 25° C. for 2 hours, and subsequently stirred at 7° C. for one night. The solution was subjected to ultrafiltration by using an XM 300 membrane and a CBS buffer solution (pH 8.5) to obtain 1 ml of liposomes in which the DTSSP was bonded to the HSA on the liposome. Then, 50 μg of the glycosylamine compound of the 3-fucosyllactose trisaccharide was added to the liposome solution. The obtained solution was stirred at 25° C. for 2 hours, and subsequently stirred at 7° C. for one night. The solution was then subjected to ultrafiltration by using an XM 300 membrane and a PBS buffer solution (pH 7.2) to bond the 3-fucosyllactose trisaccharide to the DTSSP on the human serum albumin bonded on the liposome membrane surface. In this manner, 3 types of liposomes (2 ml each), differing in the amount of sugar chain bonded thereto (referred to as 3FL-1 (50 μg), 3FL-2 (200 μg), and 3FL-3 (1 mg)), in which the 3-fucosyllactose trisaccharide is bonded to the liposome through human serum albumin (FIG. 4) (total lipid mass: 2 mg, total protein mass: 200 μg, average particle size: 100 nm), were obtained.

EXAMPLE 8

Bonding of Lewis X Trisaccharide to Human Serum Albumin (HSA) Bonded on Liposome Membrane Surfaces Liposomes comprising Lewis X Trisaccharide-bonded HSA on the liposome membrane surface were prepared according to the method of Example 4, with the exception that 50 μg of Lewis X trisaccharide (Calbiochem Co., USA) was used in place of the lactose disaccharide. 2 ml of the liposome (LX), in which Lewis X trisaccharide is bonded to the liposome through human serum albumin (FIG. 5) (total lipid mass: 2 mg, total protein mass: 200 μg, average particle size: 100 nm), was obtained.

EXAMPLE 9

Bonding of Sialyl Lewis X Tetrasaccharide to Human Serum Albumin (HSA) Bonded on Liposome Membrane Surfaces Liposomes comprising sialyl Lewis X tetrasaccharide-bonded HSA on the liposome membrane surface were prepared according to the method of Example 5, with the exception that 50 μg of sialyl Lewis X tetrasaccharide (Cal biochem Co., USA) was used in place of the 2'-fucosyllactose trisaccharide. 2 ml of the liposome (SLX), in which sialyl Lewis X tetrasaccharide is bonded to the liposome through human serum albumin (FIG. 6) (total lipid mass: 2 mg, total protein mass: 200 μg, average particle size: 100 nm), was obtained.

EXAMPLE 10

Bonding of 3'-Sialyllactosamine Trisaccharide to Human Serum Albumin (HSA) Bonded on Liposome Membrane Surfaces Liposomes comprising 3'-sialyllactosamine trisaccharide-bonded HSA on the liposome membrane surface were prepared according to the method of Example 6, with the exception that 50 μg of 3'-sialyllactosamine trisaccharide (Seikagakukogyou Co., Japan) was used in place of the difucosyllactose tetrasaccharide. 2 ml of the liposome (3SLN), in which 3'-sialyllactosamine trisaccharide is bonded to the liposome through human serum albumin (FIG. 7) (total lipid mass: 2 mg, total protein mass: 200 μg, average particle size: 100 nm), was obtained.

EXAMPLE 11

Bonding of 6'-Sialyllactosamine Trisaccharide to Human Serum Albumin (HSA) Bonded on Liposome Membrane Surfaces Liposomes comprising 6'-sialyllactosamine trisaccharide-bonded HSA on the liposome membrane surface were prepared according to the method of Example 7, with the exception that 50 μg of 6'-sialyllactosamine trisaccharide (Seikagakukogyou Co., Japan) was used in place of the 3-fucosyllactose trisaccharide. 2 ml of the liposome (6SLN), in which 6'-sialyllactosamine trisaccharide is bonded to the liposome through human serum albumin (FIG. 8) (total lipid mass: 2 mg, total protein mass: 200 μg, average particle size: 100 nm), was obtained.

EXAMPLE 12

Bonding of Tris (Hydroxymethyl) Aminomethane to Human Serum Albumin (HSA) Bonded on Liposome Membrane Surfaces For preparing a liposome as a comparative sample, 1 mg of 3,3'-dithiobis (sulfosuccinimidyl propionate) (DTSSP; Pierce Co., USA) serving as a crosslinking reagent was added to 1 ml of a part of the liposome solution obtained in Example 3. The obtained solution was stirred at 25° C. for 2 hours, and subsequently stirred at 7° C. for one night. The solution was then subjected to ultrafiltration by using an XM 300 membrane and a CBS buffer solution (pH 8.5) to obtain 1 ml of liposome in which the DTSSP was bonded to the HSA on the liposome. Then, 13 mg of tris (hydroxymethyl) aminomethane (Wako Co., Japan) was added to the liposome solution. The obtained solution was stirred at 25° C. for 2 hours, and subsequently stirred at 7° C. for one night. Then, the solution was subjected to ultrafiltration by using an XM 300 membrane and a PBS buffer solution (pH 7.2) to bond the tris (hydroxymethyl) aminomethane to the DTSSP on the human serum albumin bonded on the liposome membrane surface. In this process, an excess amount of tris (hydroxymethyl) aminomethane, that is 13 mg, already exists. Thus, the hydrophilization of the human serum albumin (HSA) bonded on the liposome membrane surface was simultaneously completed. In this manner, 2 ml of the liposome as the comparative sample (TRIS) in which the tris (hydroxymethyl) aminomethane is bonded to human serum albumin (FIG. 9) (total lipid mass: 2 mg, total protein mass: 200 μg, average particle size: 100 nm) was obtained.

EXAMPLE 13

Hydrophilization of Human Serum Albumin Bonded on Liposome Membrane Surfaces

For the 16 types of sugar-modified liposomes prepared in Examples 4 to 11, the respective HSA protein surfaces were separately hydrophilized through the following process. 13 mg of tris (hydroxymethyl) aminomethane was added to each of the 16 types of sugar-modified liposomes (2 ml each). The respective obtained solutions were stirred at 25° C. for 2 hours, and subsequently stirred at 7° C. for one night. The solutions were then subjected to ultrafiltration by using an XM 300 membrane and a PBS buffer solution (pH 7.2) to remove unreacted materials. In this manner, 2 ml of final product for each of the 16 types of hydrophilized sugar-modified liposome complexes (LAC-1, LAC-2, LAC-3, 2FL-1, 2FL-2, 2FL-3, DFL-1, DFL-2, DFL-3, 3FL-1, 3FL-2, 3FL-3, LX, SLX, 3SLN and 6SLN) (total lipid mass: 2 mg, total protein mass: 200 μg, average particle size: 100 nm) were obtained.

EXAMPLE 14

Measurement of Lectin-Binding Activity Inhibiting Effect in Each Type of Sugar-Modified Liposome Complex The in vitro lectin-binding activity of each of the 16 types of hydrophilized sugar-modified liposomes prepared in Example 13 was measured through an inhibition test using a lectin-immobilized microplate by methods known in the art (see, e.g., Yamazaki, N., et al., *Drug Delivery System*, 14:498–505 (1999)). More specifically, a lectin (E-selectin; R&D Systems Co., USA) was immobilized on a 96 well-microplate. Then, 0.1 μg of biotinylated and fucosylated fetuin as a comparative ligand, and various types of sugar-modified liposome complexes having different densities (each including 0.01 μg, 0.04 μg, 0.11 μg, 0.33 μg or 1 μg of protein), were placed on the lectin-immobilized plate, and incubated at 4° C. for 2 hours. After washing with PBS (pH 7.2) three times, horseradish peroxidase (HRPO)-conjugated streptavidin was added to each of the wells. The respective test solutions were incubated at 4° C. for 1 hour, and then washed with PBS (pH 7.2) three times. Then, peroxidase substrates were added to the test solutions, and incubated at room temperature. Then, the absorbance at 405 nm of each of the test solutions was determined by a microplate reader (Molecular Devices Corp., USA). For the biotinylation of the fucosylated fetuin, each of the test solutions was subject to a sulfo-NHS-biotin reagent (Pierce Chemical Co., USA) treatment and refined by using a Centricon-30 (Amicon Co., USA). HRPO-conjugated streptavidin was prepared by oxidizing HRPO and bonding streptavidin to the oxidized HRPO through a reductive amination method using $NaBH_3CN$. This measurement result is shown in Table 1.

TABLE 1

Test Result showing Lectin-Binding Activity Inhibiting Effect of Each Type of Sugar-Modified Liposome Complex

| Liposome Complex | Inhibiting Effect (absorbance) at each density of liposome complexes (μg protein) | | | | |
|---|---|---|---|---|---|
| | 0.01 μg | 0.04 μg | 0.11 μg | 0.33 μg | 1 μg |
| LAC-1 | 0.115 | 0.114 | 0.112 | 0.112 | 0.105 |
| LAC-2 | 0.112 | 0.109 | 0.104 | 0.104 | 0.097 |
| LAC-3 | 0.119 | 0.118 | 0.112 | 0.109 | 0.108 |
| 2FL-1 | 0.121 | 0.115 | 0.106 | 0.097 | 0.067 |
| 2FL-2 | 0.131 | 0.119 | 0.116 | 0.111 | 0.079 |
| 2FL-3 | 0.149 | 0.133 | 0.122 | 0.104 | 0.073 |
| DFL-1 | 0.167 | 0.158 | 0.146 | 0.131 | 0.108 |
| DFL-2 | 0.136 | 0.134 | 0.133 | 0.120 | 0.106 |
| DFL-3 | 0.163 | 0.150 | 0.134 | 0.118 | 0.097 |
| 3FL-1 | 0.138 | 0.131 | 0.121 | 0.113 | 0.085 |
| 3FL-2 | 0.148 | 0.134 | 0.128 | 0.123 | 0.092 |
| 3FL-3 | 0.149 | 0.134 | 0.129 | 0.128 | 0.110 |
| LX | 0.199 | 0.195 | 0.195 | 0.195 | 0.129 |
| SLX | 0.105 | 0.100 | 0.100 | 0.084 | 0.073 |
| 3SLN | 0.175 | 0.158 | 0.144 | 0.131 | 0.095 |
| 6SLN | 0.256 | 0.245 | 0.233 | 0.200 | 0.151 |

EXAMPLE 15

$^{125}$I-Labeling of Each Type of Sugar-Modified Liposome through the Chloramine T Method A chloramine T (Wako Pure Chemical Co., Japan) solution and a sodium disulfite solution were prepared at 3 mg/ml and 5 mg/ml, respectively. 50 μl of the 16 different types of hydrophilized sugar-modified liposomes prepared in Example 13, and the liposome of Example 12, were put into separate Eppendorf tubes. Then, 15 μl of $^{125}$I-NaI (NEN Life Science Product, Inc. USA) and 10 μl of chloramine T solution were added thereto and reacted therewith. 10 μl of chloramine T solution was added to the respective solutions every 5 minutes. After 15 minutes from the completion of the above procedure repeated twice, 100 μl of sodium disulfite serving as a reducer was added to the solutions to stop the reaction. Then, each of the resulting solutions was placed on a Sephadex G-50 (Phramacia Biotech. Sweden) column chromatography, and eluted by PBS to purify a labeled compound. Finally, a non-labeled liposome complex was added to each of the solutions to adjust a specific activity ($4 \times 10^6$ Bq/mg protein). In this manner, 16 types of $^{125}$I-labeled liposome solutions were obtained.

EXAMPLE 16

Measurement of Transfer Rate of Each Type of Sugar-Modified Liposome Complex to Tissues of Mice with Cancer Using an oral sonde, 13 of the different types of $^{125}$I-labeled, hydrophilized sugar-modified liposomes of Example 15 (LAC-1, LAC-2, LAC-3, 2FL-1, 2FL-2, 2FL-3, DFL-1, DFL-2, DFL-3, 3FL-1, 3FL-2, 3FL-3 and TRIS) (equivalent to 3 μg of protein per mouse) were administered to male ddY mice (7 weeks of age) which had abstained from food, except for water, for one whole day, in an amount of 0.2 ml which is equivalent to 3 μg of protein per mouse. After 10 minutes, 1 ml of blood was taken from descending aorta under Nembutal anesthesia. Then, $^{125}$I-radioactivity in the blood was measured with a gamma counter (Aloka ARC 300). Further, in order to check the in vivo stability of each type of liposome complex, serum from each mouse's blood was subjected to chromatography using a Sephadex G-50. As a result, most of the radioactivity in each sample of serum was found in void fractions having a high molecular weight, and it was proved that each type of liposome complexes has a high in vivo stability. The radioactivity transfer rate from intestine to blood was represented by the ratio of the radioactivity per ml of blood to the total of given radioactivity (% dose/ml blood). This measurement result is shown in FIGS. 10 to 13.

EXAMPLE 17

Measurement of Distribution Rate of Each Type of Sugar-Modified Liposome Complex to Tissues of Mice with Cancer Ehrlich ascites tumor (EAT) cells (about $2 \times 10^7$ cells) were implanted subcutaneously into the femoral region in male ddY mice (7 weeks of age), and the mice were used in this test after the tumor tissues grew to 0.3 to 0.6 g (after 6 to 8 days). Five of the different types of $^{125}$I-labeled, hydrophilized sugar-modified liposome complexes (LX, SLX, 3SLN, 6SLN and TRIS) of Example 15 were injected into the tail veins of the mice in an amount of 0.2 ml which is equivalent to 3 μg of protein per mouse. After 60 minutes, tissues (blood, liver, spleen, lung, brain, inflammatory tissues around cancer, cancer and lymph node) were extracted, and the radioactivity of each of the extracted tissues was measured with a gamma counter (Aloka ARC 300). The distribution rate of the radioactivity in each of the tissues was represented by a ratio of the radioactivity per gram of each of the tissues to the total of given radioactivity (% dose/g tissue). This measurement result is shown in FIGS. 14 to 21.

The results from these experiments show that the sugar-modified liposomes of the present invention are innovative in that they are excellent in intestinal absorption and are capable of being administered via the intestine, which has not been found in conventional liposome related products. In addition, the intestinal absorption can be controlled by adjusting the identity and amount of the sugar chain bonded to the liposomes.

Furthermore, the in vivo mobility of sugar-modified liposomes of the present invention, and their ability to target selected tissues in vivo, can be facilitated or suppressed in a living body by utilizing the difference in the molecular structure of the sugar chain, and varying their amounts.

Thus, the sugar-modified liposomes of the present invention can be used to deliver drugs or genes through the intestine efficiently and safely without any side effects. They may also be used as an effective delivery mechanism for selectively delivering drugs or genes to target tissues such as blood, liver, spleen, lung, brain, cancer tissues, inflammatory tissue, or lymph node, and can be used in DDS materials in light of their enhanced mobility. Thus, the liposomes of the present invention are useful particularly in the medical and pharmaceutical fields.

What is claimed is:
1. A liposome comprising:
   (a) at least one sugar chain bonded to the membrane surface of the liposome; and
   (b) a hydrophilizing moiety bonded to the membrane surface of the liposome in addition to the sugar chain;
   wherein the hydrophilizing moiety is tris (hydroxymethyl) aminomethane.

2. The liposome as defined in claim 1, wherein the hydrophilizing moiety is bonded directly to the membrane surface of the liposome.

3. The liposome as defined in claim 1, further comprising a linker protein bonded to the membrane surface of the liposome, wherein the sugar chain is bonded to the membrane surface of the liposome through the linker protein.

4. The liposome as defined in claim 3, further comprising an additional hydrophilizing moiety bonded to the linker protein in addition to the sugar chain.

5. The liposome as defined in claim 4, wherein the hydrophilizing moiety bonded to the linker protein is the same as the hydrophilizing moiety bonded to the membrane surface of the liposome.

6. The liposome as defined in claim 3, wherein the linker protein is human serum albumin or bovine serum albumin.

7. The liposome as defined in claim 1, wherein the sugar chain is selected from the group consisting of: lactose, 2'-fucosyllactose trisaccharide, difucosyllactose tetrasaccharide, 3-fucosyllactose trisaccharide, Lewis X trisaccharide, sialyl Lewis X tetrasaccharide, 3'-sialyllactosamine trisaccharide, and 6'-sialyllactosamine trisaccharide.

8. The liposome as defined in claim 1, wherein the sugar chain is bonded to the membrane surface of the liposome at a density level whereby the liposome can efficiently deliver a drug to target cells and tissues with reduced side effects.

9. A liposome product comprising the liposome as defined in any one of claims 1–8, and a drug, gene, or cosmetic encapsulated in the liposome.

10. A liposome comprising:
  (a) at least one sugar chain bonded to the membrane surface of the liposome;
  (b) a hydrophilizing moiety bonded to the membrane surface of the liposome in addition to the sugar chain;
  (c) a linker protein bonded to the membrane surface of the liposome, wherein the sugar chain is bonded to the membrane surface of the liposome through the linker protein; and
  (d) an additional hydrophilizing moiety bonded to the linker protein in addition to the sugar chain.

11. The liposome as defined in claim 10, wherein the hydrophilizing moiety bonded to the linker protein is the same as the hydrophilizing moiety bonded to the membrane surface of the liposome.

12. The liposome as defined in claim 10, wherein the linker protein is human serum albumin or bovine serum albumin.

13. The liposome as defined in claim 10, wherein the sugar chain is selected from the group consisting of: lactose, 2'-fucosyllactose trisaccharide, difucosyllactose tetrasaccharide, 3-fucosyllactose trisaccharide, Lewis X trisaccharide, sialyl Lewis X tetrasaccharide, 3'-sialyllactosamine trisaccharide, and 6'-sialyllactosamine trisaccharide.

14. The liposome as defined in claim 10, wherein the sugar chain is bonded to the membrane surface of the liposome at a density level whereby the liposome can efficiently deliver a drug to target cells and tissues with reduced side effects.

15. A liposome product comprising the liposome as defined in any one of claims 10–13, and a drug, gene, or cosmetic encapsulated in the liposome.

* * * * *